(12) United States Patent
Ihn (10) Patent No.: US 8,015,877 B2
(45) Date of Patent: Sep. 13, 2011

(54) IMAGING AN ANOMALY USING BACKSCATTERED WAVES

(75) Inventor: Jeong-Beom Ihn, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 634 days.

(21) Appl. No.: 12/103,118

(22) Filed: Apr. 15, 2008

(65) Prior Publication Data

US 2009/0032329 A1 Feb. 5, 2009

Related U.S. Application Data

(63) Continuation of application No. 11/749,539, filed on May 16, 2007, now Pat. No. 7,891,247.

(51) Int. Cl.
*G01N 29/04* (2006.01)

(52) U.S. Cl. ............... 73/603; 73/597; 73/598; 73/602; 73/606; 73/799

(58) Field of Classification Search .............. 73/12.01, 73/603, 606, 799, 801, 802, 598, 600, 602, 73/597
See application file for complete search history.

(56) References Cited

U.S. PATENT DOCUMENTS

| | | | |
|---|---|---|---|
| 4,187,725 A | 2/1980 | Gavrev et al. | |
| 4,299,128 A * | 11/1981 | Gruber | 73/627 |
| 4,546,652 A | 10/1985 | Virkar et al. | 73/776 |
| 4,574,637 A * | 3/1986 | Adler et al. | 73/629 |
| 4,658,649 A | 4/1987 | Brook | |
| 4,817,016 A | 3/1989 | Thompson et al. | |
| 4,866,614 A | 9/1989 | Tam | |
| 5,184,516 A * | 2/1993 | Blazic et al. | 73/799 |
| 5,760,904 A * | 6/1998 | Lorraine et al. | 356/513 |
| 5,841,031 A | 11/1998 | Chung | |
| 5,987,994 A | 11/1999 | Maltby et al. | |
| 6,128,092 A * | 10/2000 | Levesque et al. | 356/451 |
| 6,311,565 B1 | 11/2001 | Hinz et al. | |
| 6,772,638 B2 | 8/2004 | Matney et al. | |

(Continued)

FOREIGN PATENT DOCUMENTS

JP 2001215218 8/2001

(Continued)

OTHER PUBLICATIONS

International Search Report, corresponding to International Patent Application No. PCT/US2008/063639, dated Nov. 10, 2008.

(Continued)

*Primary Examiner* — Jacques M Saint Surin
(74) *Attorney, Agent, or Firm* — Charles L. Moore; Moore & Van Allen PLLC (57) ABSTRACT

A method for generating an image of an anomaly may include generating a pulse wave into a structure being evaluated from each of a plurality of sensors and collecting any scattered wave data caused by the pulse wave impacting an anomaly. The scattered wave data may be collected by the same sensor that generated the pulse wave or by a different sensor. The method may also include identifying any backscattered wave data from a distal edge or border of any anomaly relative to a location of the sensor collecting the scattered wave data. The method may additionally include processing the backscattered wave data from each of the sensors collecting the scattered wave data to generate a two dimensional image of any anomaly. The method may further include presenting the two dimensional image of any anomaly.

25 Claims, 5 Drawing Sheets

U.S. PATENT DOCUMENTS

| | | | |
|---|---|---|---|
| 7,024,315 B2 * | 4/2006 | Giurgiutiu | 702/33 |
| 7,231,304 B2 * | 6/2007 | Mitchell | 702/35 |
| 7,263,888 B2 * | 9/2007 | Barshinger et al. | 73/606 |
| 7,333,898 B2 * | 2/2008 | Griess et al. | 702/35 |
| 7,367,236 B2 | 5/2008 | Georgeson et al. | |
| 7,388,365 B2 * | 6/2008 | Nokuo et al. | 324/158.1 |
| 7,552,027 B2 * | 6/2009 | Kearns et al. | 702/182 |
| 2003/0009300 A1 | 1/2003 | Giurgiutiu | |
| 2004/0206181 A1 | 10/2004 | Coen et al. | |
| 2005/0068041 A1 | 3/2005 | Kress et al. | |
| 2007/0017297 A1 | 1/2007 | Georgeson et al. | |
| 2008/0283332 A1 | 11/2008 | Ihn | |
| 2009/0032329 A1 | 2/2009 | Ihn | |
| 2009/0192729 A1 | 7/2009 | Pado et al. | |

FOREIGN PATENT DOCUMENTS

| | | |
|---|---|---|
| JP | 2005300274 | 10/2005 |
| WO | 2006009669 | 1/2006 |

OTHER PUBLICATIONS

Written Opinion, corresponding to International Patent Application No. PCT/US2008/063639, dated Nov. 10, 2008.

International Search Report, corresponding to International Patent Application No. PCT/US2009/036188, dated Mar. 22, 2010.

Written Opinion, corresponding to International Patent Application No. PCT/US2009/036188, dated Mar. 22, 2010.

Kress, K-P et al. "Smart Wide-Area Imaging Sensor System (SWISS)." Proceedings of the SPIE—The International Society for Optical Engineering, SPIE, US, vol. 4332, Mar. 2001, pp. 490-496.

European Patent Office, European Extended Search Report for Application No. 10193287.9 dated Mar. 18, 2011.

* cited by examiner

IMAGING AN ANOMALY USING BACKSCATTERED WAVES

CROSS-REFERENCE TO RELATED APPLICATIONS

This application is a continuation-in-part of application Ser. No. 11/749,539, filed May 16, 2007 now U.S. Pat. No. 7,891,247, and entitled "METHOD AND SYSTEM FOR DETECTING AN ANOMALLY AND DETERMINING ITS SIZE."

BACKGROUND OF THE INVENTION

The present disclosure relates to detecting anomalies in a structure, such as an aircraft or other structure, and more particularly to a method and system for detecting an anomaly, such as a delamination or other defect, and generating an image of the anomaly using backscattered waves.

New, lightweight composite materials and designs are being used more extensively in the aerospace industry for commercial aircraft and other aerospace vehicles, as well as in other industries. The structures using these composite materials may be formed using multiple plies or layers of material that may be laminated together to form a lightweight, high strength structure. Similar to traditional materials, these structures may be subject to extreme stresses, such as during flight operations for aerospace vehicles or other operations, or damage from an impact or other cause. The multiple plies of material can separate or become delaminated as a result of these stresses or impact. As new and traditional materials are being designed in more optimized manner, there is also the need in the aerospace industry to quickly identify and maintain all structures with better efficiency—improving the dispatch reliability and increasing the in-service use of aircraft and any other similar expensive equipment. As such, there is a need to visualize damage or delamination in plate-like structures using permanently attached piezoelectric actuators/sensors. However, such efforts have failed to successfully demonstrate feasibility of actual implementation on real aircraft structures due to heavy dependency on empirical imaging processes based on prior training data and lack of simple but robust interpretation techniques directly relating complex signal responses to true damage information. Previous imaging techniques have only generated qualitative images of damage which were not directly related to the true damage size or outline. Accordingly, a robust imaging technique is needed that can generate a true image of damage equivalent to the one from conventional non-destructive evaluation methods, such as C-scan, x-ray or similar evaluation technique.

BRIEF SUMMARY OF THE INVENTION

In accordance with an embodiment of the present disclosure, a method for generating an image of an anomaly may include generating a pulse wave into a structure being evaluated from each of a plurality of sensors and collecting any scattered wave data caused by the pulse wave impacting an anomaly. The scattered wave data may be collected by the same sensor that generated the pulse wave or by a different sensor. The method may also include identifying any backscattered wave data from a distal edge or border of any anomaly relative to a location of the sensor collecting the scattered wave data. The method may additionally include processing the backscattered wave data from each of the sensors collecting the scattered wave data to generate a two dimensional image of any anomaly. The method may further include presenting the two dimensional image of any anomaly.

In accordance with another embodiment of the present, a method for generating an image of an anomaly may include generating a pulse wave into a structure being evaluated from each of a plurality of sensors positioned at predetermined locations on a portion of the structure being evaluated. The method may also include collecting any scattered wave data caused by the pulse wave impacting an anomaly. The scattered wave data may be collected by the same sensor that generated the pulse wave or by a different sensor. The method may also include identifying any backscattered wave data from a distal edge of any anomaly relative to a location of the sensor collecting the scattered wave data. The method may additionally include processing the backscattered wave data from each of the sensors collecting the scattered wave data to generate a two dimensional image of any anomaly in the structure being evaluated. Processing the backscattered wave data may include superimposing the backscattered wave data from each of the sensors that collected the scattered wave data. An outline of any anomaly corresponds to an area of most overlapping backscattered wave data which appears visually contrasted relative to other portions in the two dimensional image of the structure being evaluated. The method may further include presenting the two dimensional image of any anomaly.

In accordance with another embodiment of the present disclosure, a system for generating an image of an anomaly may include a plurality of devices. Each device may generate a pulse wave into a structure being evaluated and may collect any scattered wave data caused by energy of the pulse wave being at least partially reflected by any anomaly. The system may also include a structural health monitoring unit for generating a two dimensional image of any anomaly in the structure being evaluated from backscattered wave data from a distal edge of any anomaly relative to a location of the device collecting the scattered wave data.

In accordance with another embodiment of the present disclosure, a system for generating an image of an anomaly may include a plurality of actuators. Each actuator may be positioned at a predetermined location on a portion of a structure being evaluated. Each actuator may generate a pulse wave into the structure. A plurality of sensors may each be positioned at a selected location on the portion of the structure being evaluated. Each sensor may collect any scattered wave data caused by energy of the pulse wave being at least partially reflected by any anomaly. The system may also include a structural health monitoring unit for identifying any backscattered wave data from a distal edge of any anomaly relative to the sensor collecting the scattered wave data. The structural health monitoring unit may also process the backscattered wave data from each of the sensors collecting the scattered wave data to generate a two dimensional image of any anomaly. The system may further include an output device for presenting the two dimensional image of any anomaly.

Other aspects and features of the present disclosure, as defined solely by the claims, will become apparent to those ordinarily skilled in the art upon review of the following non-limited detailed description of the disclosure in conjunction with the accompanying figures.

DETAILED DESCRIPTION OF THE INVENTION

The following detailed description of embodiments refers to the accompanying drawings, which illustrate specific embodiments of the disclosure. Other embodiments having different structures and operations do not depart from the scope of the present disclosure.

Figure 1:
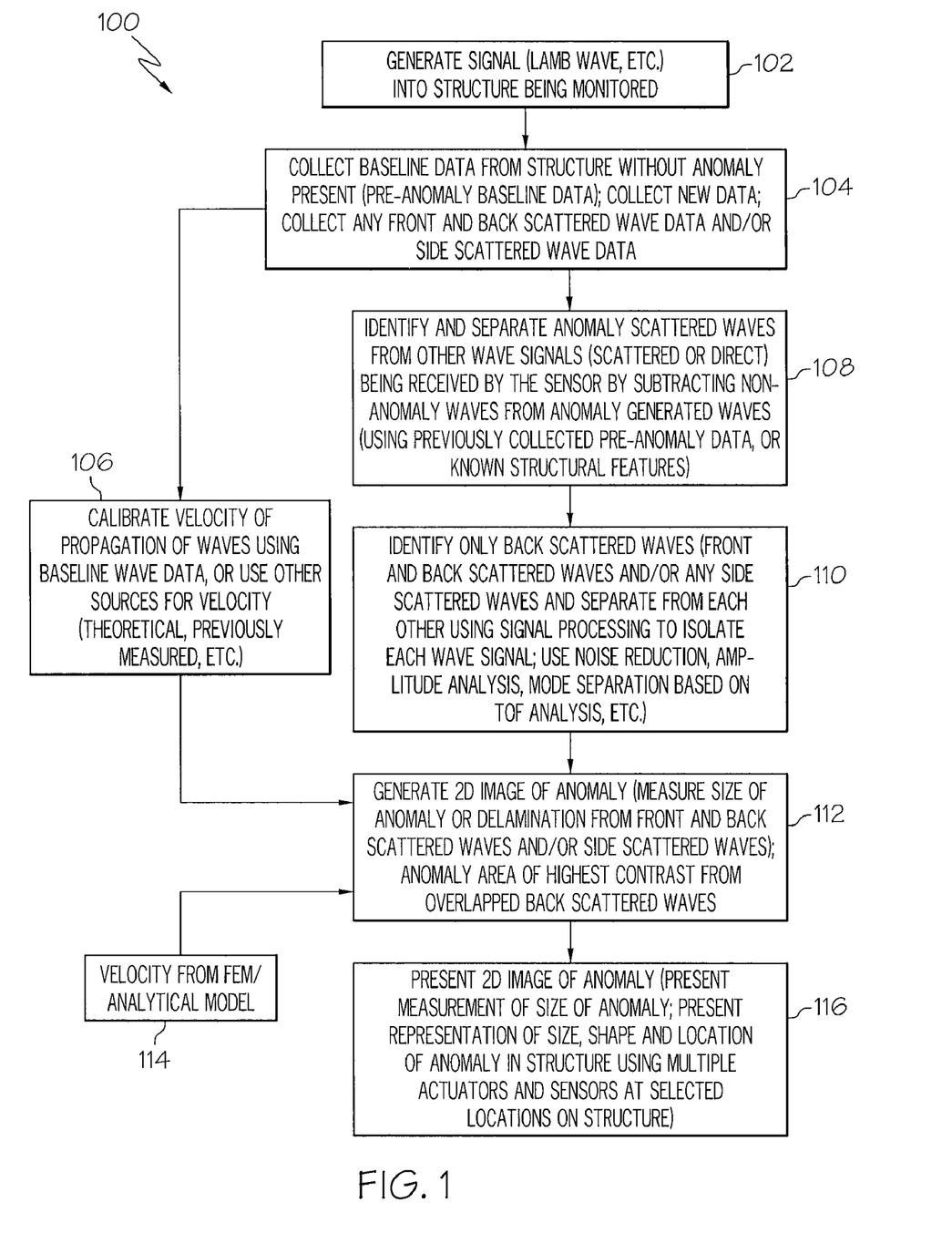
FIG. 1 is a flow chart of an example of a method for generating an image of an anomaly in a structure in accordance with an embodiment of the present disclosure.
Figure 2:
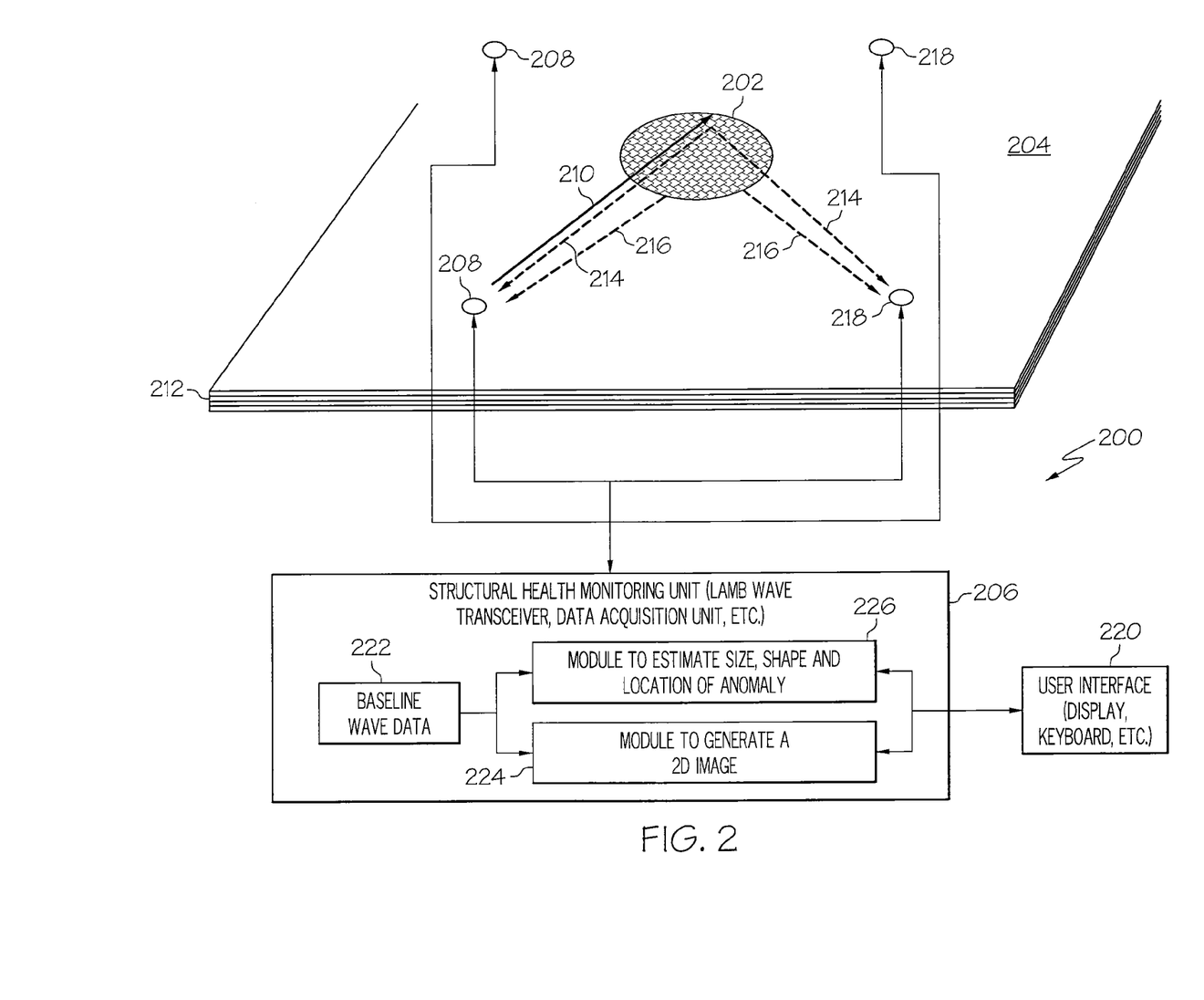
FIG. 2 is a block diagram of an exemplary system for generating an image of an anomaly in a structure in accordance with an embodiment of the present disclosure.

FIG. 1 is a flow chart of an example of a method 100 for generating an image of an anomaly in a structure in accordance with an embodiment of the present disclosure. In block 102, a pulse wave, lamb wave or similar signal may be generated and directed into a structure being monitored or evaluated. Lamb waves may be used for detecting and determining the size of an anomaly because they are similar to longitudinal waves and include compression and rarefraction but are bounded by the surface of the structure into which they are transmitted causing a wave-guide effect. For easier and more robust imaging process, a single mode of Lamb waves or similar pulse wave (i.e. a0 fundamental asymmetric mode or s0 fundamental symmetric mode) may be injected into a structure Referring also to FIG. 2, FIG. 2 is a block diagram of an exemplary system 200 for generating an image of an anomaly 202 in a structure 204 in accordance with an embodiment of the present disclosure. A structural health monitoring unit 206 may be used to generate the pulse wave. A plurality of sensors or actuators 208 may each generate, transfer or direct a pulse wave, illustrated by arrow 210 in FIG. 2, into the structure 204 or object being monitored. As described herein in more detail, any scattered wave data caused by the pulse wave 210 impacting the anomaly 202 may be collected by the same sensor 208 that generated the pulse wave or by a different sensor 218. The structural health monitoring unit 206 may be a lamb wave generator or transceiver, or data acquisition unit capable of transmitting and receiving signals for structural health monitoring as described herein, or a similar device.

In accordance with another embodiment of the present disclosure, the sensors 208 may each be a combination actuator and sensor for both generating the pulse wave and receiving any scattered wave data by the same actuator-sensor that generated the pulse wave. The actuator or combination actuator-sensor 208 may be an electromechanical actuator/sensor capable of generating or directing a signal for structural health monitoring, such as a lamb wave or similar signal or wave, into the structure 204. An example of the actuator or combination actuator-sensor 208 may be a piezoelectric actuator/sensor or similar device attachable to the structure 204.

The structure 204 or object may be formed by a plurality 212 of plies or layers of composite material or similar material. The structure 204 or object may be a vehicle, such as an aerospace vehicle, terrestrial vehicle, watercraft, civil structure, such as a bridge, building or other structure, or any object were monitoring the structural health or condition is desired.

Referring back to FIG. 1, in block 104, baseline wave data for the structure 204 may be collected without any anomaly. The baseline wave data may be collected before the structure 204 or object is placed in service or at some point in time before beginning a structural health monitoring program on the structure 204.

Also in block 104, new data may be collected after collecting the baseline wave data by generating a new pulse wave 210. Any scattered wave data caused by the pulse wave 210 impacting an anomaly, such as anomaly 202 or delamination in the example of FIG. 2 may be collected. Lamb waves with a sufficiently short wavelength impinging upon an anomaly, such as a delamination in a layered structure like structure 204, will result in wave scattering. The wave scattering results in a complex response that requires processing as described herein to generate an image. The wavelength of impinging waves can be adjusted based on the range of damage size to be detected. For example, a wavelength range of about 0.4 inches to about 0.8 inches may detect an anomaly have a diameter or linear dimension of about 0.5 inches to about 2 inches. A numerical simulation by FEM (Finite Element Method) and other tests have indicated that the dominant scattered wave around a delamination may be the backscattered wave or wave scattered from a back or distal edge or border of a delamination relative to a location or position of the sensor collecting the backscattered wave data. As described with reference to FIG. 2, the backscattered wave 214 may be a stronger scattered wave than a front scattered wave 216 as the wave travels from inside the anomaly 202 or delamination to outside the area of the anomaly 202. While backscattered wave data may be of primary interest both front scattered wave data 216 and backscattered wave data 214 may be collected. The backscattered wave data 214 or pulses may be collected by the combination actuator-sensor 208 if the actuator-sensor 208 is self-sensing. The backscattered wave data 214 or pulses may also be collected by a sensor 218 different from the sensor 208 or actuator that generated the pulse wave. The sensor 218 is capable of receiving the scattered wave data or pulses and transmitting the received or collected scattered wave data to the structural health monitoring unit 206 for analysis and to generate a two dimensional image of the anomaly 202. The sensor 218 may also be an electromechanical device, such as a piezoelectric sensor or similar device capable of sensing the front scattered waves 216 and the backscattered waves 214.

The system 200 may include actuators 208 without a sensing capability and sensors 218 in what may be referred to as a pitch-catch configuration or pitch-catch actuators/sensors and may operate in a pitch-catch mode. The actuators 208 may transmit or pitch pulse waves 210 into the structure 204 and the sensors 218 may receive or catch any backscattered wave data 214 and front scattered wave data 216 from any anomaly 202. An example of a pitch-catch configuration or a pitch-catch mode of operation to generate a two dimensional image will be described in more detail with reference to FIGS. 4A-4E.

Alternatively, as described above, the devices 208 and 218 may both be combination actuator and sensor devices for both transmitting the pulse wave 210 and receiving the backscattered wave data 214 and front scattered wave data 216. The devices 208 and 218 send the collected data to the structural health monitoring unit 206 to identify the backscattered wave data 214 and to generate the two dimensional image of the anomaly 202. This arrangement may be referred to as a pulse-echo arrangement or pulse-echo actuators/sensors and may operate in a pulse-echo mode or self-sensing mode. An example of a pulse-echo configuration or pulse-echo mode of operation will be described in more detail with reference to FIG. 5.

Any combination of multiple pitch-catch actuators/sensors or pulse-echo actuators/sensors 208 and 218 may be positioned at predetermined locations on the structure 204 being evaluated to generate the two dimensional image of the anomaly 202. The combination actuator and sensor devices may also operate in a pitch-catch mode. A plurality of self-sensing sensors 208 or pitch-catch actuators and sensors 208 and 218 are needed to generate the two dimensional image of the anomaly 202.

Figure 3:
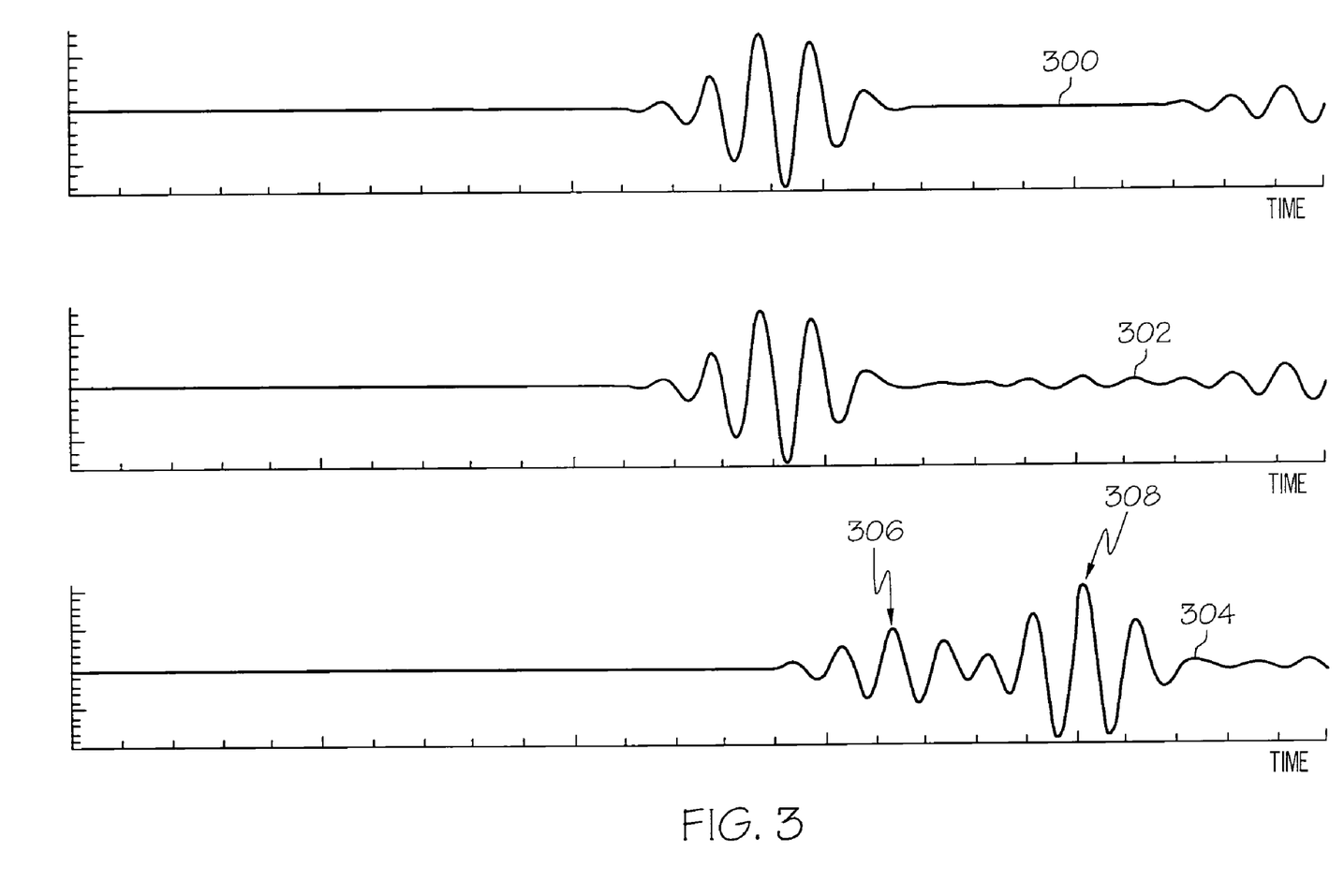
FIG. 3 is an illustration of waveforms for generating an image of an anomaly in a structure in accordance with an embodiment of the present disclosure.

In block 106, a velocity of propagation of waves or signals in the structure 204 may be measured or calibrated using the baseline wave data. An example of a baseline waveform 300 is illustrated in FIG. 3. FIG. 3 also illustrates an example of a waveform 302 illustrating detection of an anomaly and a waveform 304 illustrating front scattered wave data 306 and backscattered wave data 308. As illustrated in FIG. 3, the backscattered wave 308 exhibits a much higher amplitude than the front scattered wave 306 in a case of typical damage or an anomaly in a composite structure or layered structure similar to that illustrated in FIG. 2. The calibrated velocity of propagation of the waves may be used in generating the two dimensional image from the backscattered wave data 214 as described herein.

In block 108, signal processing may be performed on the front scattered wave data 214 and the backscattered wave data 216 using the collected baseline wave data for the structure 204. The scattered waves 214 and 216 induced by the anomaly 202 can be decoupled or separated from any other waves, such as directly transmitted waves from the actuator 208 to sensor 218 and/or other possible reflected waves from any structural boundaries or other features present in the structure 204, by subtracting post damage data from pristine (baseline) wave data.

In block 110, the backscattered waves 214 and the front scattered waves 216 may be separated or separately identified. The backscattered waves 214 and front scattered waves 216 may be separated or identified using amplitude comparison (i.e., the backscattered waves exhibit a much higher amplitude than front scattered waves in case of an anomaly in a composite structure similar to that illustrated in FIG. 3). The backscattered waves 214 and front scattered waves 216 may also be separated or identified using mode separation based on time-of-flight analysis of the signals, noise cancellation or other known signal processing techniques.

In block 112, a two dimensional image of the anomaly in the portion of the structure 204 under evaluation may be generated from the backscattered wave data 214. As described in more detail herein, the anomaly area or outline of the area may be the area of highest contrast from other areas of the portion of the structure under evaluation by overlapping or superimposing the backscattered waves from each of the sensors 208 and 218 or actuator sensor combinations. The two dimensional image may be generated using the calibrated velocity of propagation which was determined from the baseline data determined in block 106. The velocity of wave propagation from FEM or analytical models 114 may also be used as inputs in generating the two dimensional images.

In another embodiment of the present disclosure, the size of the delamination or anomaly may be estimated based on a difference in arrival time of the backscattered wave data 214 and front scattered wave data 216 at the sensors 208 and 218 or a Time-of-Flight (TOF) of the wave and based on the calibrated velocity of the wave propagation (Vg) in the structure 204. The TOF may be defined as the time from when a signal or wave is transmitted and the front and backscattered waves are respectively received. Examples of estimating damage size for different actuator/sensor configurations based on the measured Time-of-Flight information of the backscattered wave ($TOF_b$), the measured Time-of-Flight information of the front scattered ($TOF_f$) and the calibrated velocity Vg within the structure are described in more detail in U.S. application Ser. No. 11/749,539, filed May 16, 2007, and entitled "METHOD AND SYSTEM FOR DETECTING AN ANOMALY AND DETERMINING ITS SIZE," which is assigned to the same assignee as the present disclosure, is a parent application of the present application, and is incorporated herein in its entirety by reference.

Figure 5:
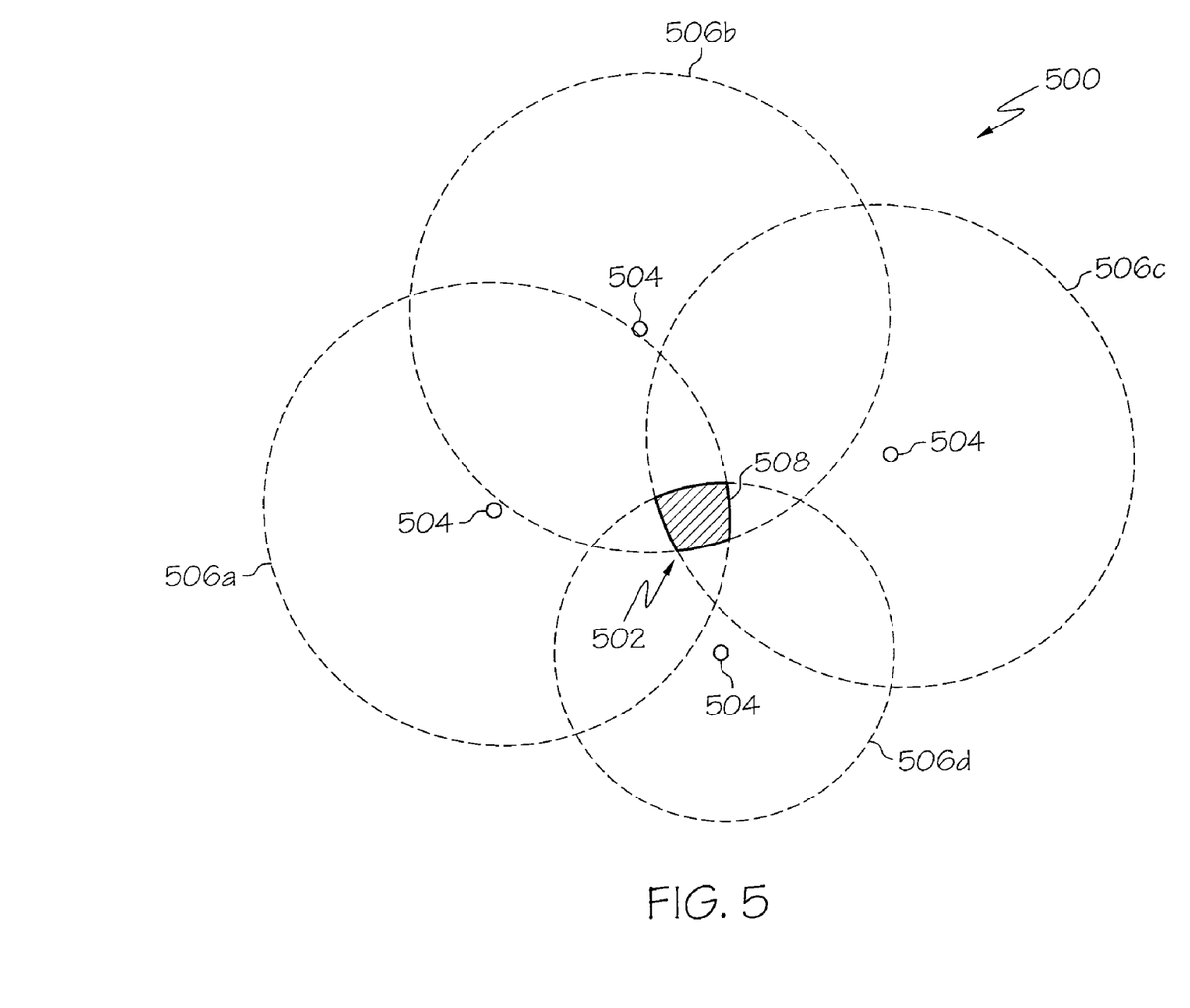
FIG. 5 illustrates an example of generating an image of an anomaly in a structure using a pulse-echo or self-sensing configuration in accordance with an embodiment of the present disclosure.

In block 116, the two dimensional image of any delamination or anomaly may be presented to a user on a display, printout or other means. Examples of presenting the two dimensional image of a delamination or other anomaly will be described with reference to FIGS. 4A-4D and FIG. 5. FIGS. 4A-4D illustrate an example of operation in a pitch-catch mode, similar to that previously described, wherein a multiplicity of substantially ellipsoid-shaped actuator-sensor pulse wave paths are generated to produce the two-dimensional image of any anomaly. FIG. 5 illustrates an example of operation in a pulse-echo mode, similar to that previously described, wherein a multiplicity of substantially circular-shaped pulse-echo pulse wave paths are generated to produce the two dimensional image of any anomaly.

Referring again to FIG. 2, the two dimensional image of the delamination or other anomaly may be presented on a user interface 220 (FIG. 2), such as a display. The user interface 220 may also include a keyboard, computer pointing device, printer, or other means for interfacing with and controlling operation of the structural health monitoring unit 206.

The structural health monitoring unit 206 may include a data storage element 222 to store the baseline wave data and any other data for analyzing the back scatter wave data 214 and the front scattered wave data 216. The structural health monitoring unit 206 may also include a module 224 to generate the two dimensional image of any delamination or anomaly as described herein. Elements of the method 100 may be embodied in the module 224 and performed thereby.

The structural health monitoring unit 206 may also include a module to estimate the size, shape and location of any delamination or anomaly as described herein.

FIGS. 4A-4E illustrate an example of generating an image 400 of an anomaly 402 in a structure using a pitch-catch configuration in accordance with an embodiment of the present disclosure. Similar to that previously described, in a pitch-catch configuration or mode of operation, selected ones of a plurality of sensors 404 may be actuators or preset to function as actuators under some test conditions. The actuators may each generate a separate pulse wave at different times into the structure being evaluated. As previously described, the pulse wave may be a Lamb wave.

Figure 4A:
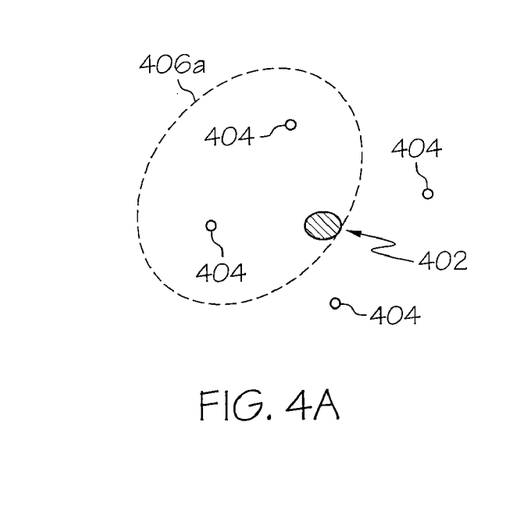
FIGS. 4A-4E illustrate an example of generating an image of an anomaly in a structure using a pitch-catch configuration in accordance with an embodiment of the present disclosure.
Figure 4B:
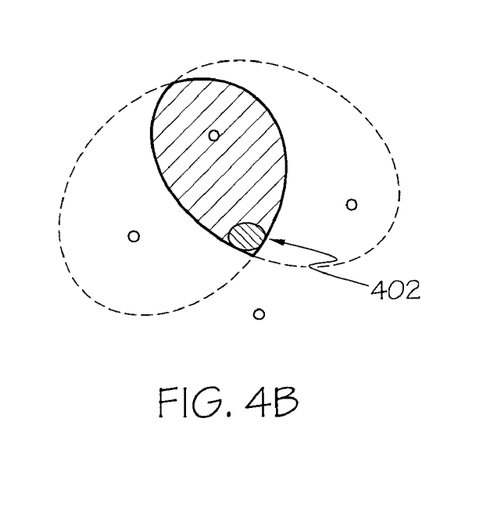
Figure 4C:
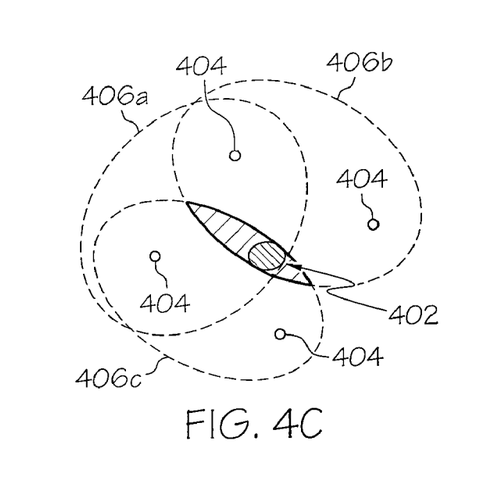
Figure 4D:
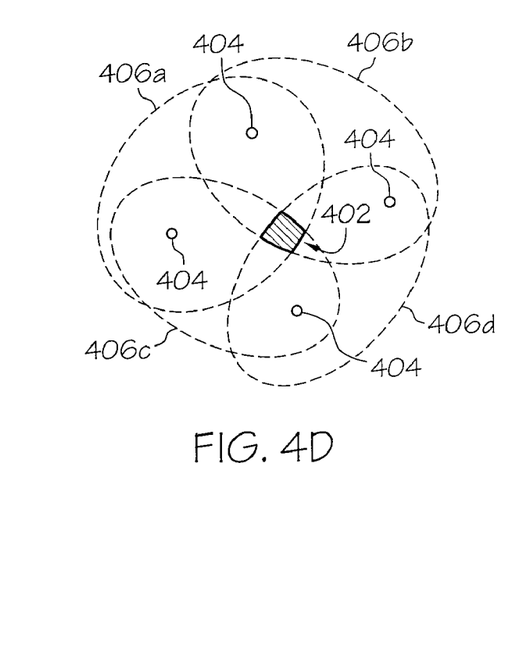
Figure 4E:
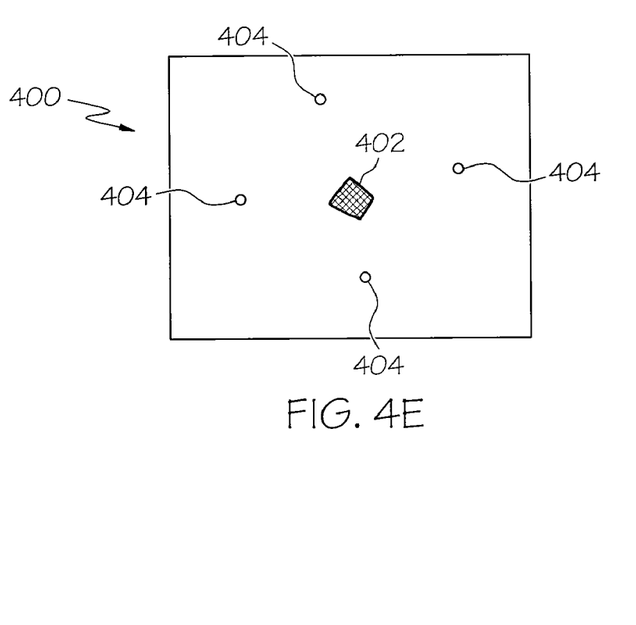

Other selected ones of the plurality of sensors 404 may collect the scattered wave data caused by the pulse wave generated by actuator sensors 404 being scattered by any anomaly or other feature of the structure being evaluated. Each of the actuators and sensors 404 may be paired to generate respective actuator-sensor wave paths 406a-406d. In the pitch-catch mode of operation the actuator-sensor wave path 406a-406d may be substantially ellipsoid-shaped as illustrated in FIGS. 4A-4D. The shape of each actuator-sensor pulse wave path 406a-406d may be determined by a wave velocity profile as a function of a wave propagation angle and a measured time-of-flight of the backscattered waves. As illustrated in FIGS. 4A-4D, each of the actuator-sensor pulse wave paths 406a-406d may be superimposed on one another over the portion of the structure being evaluated to generate the two dimensional image of any anomaly. As illustrate in FIGS. 4D and 4E, the outline of the anomaly 402 corresponds to an area of most overlapping backscattered wave data of the ellipsoid-shaped pulse wave paths. This area will appear visually contrasted as illustrated in FIG. 4E relative to other portions or areas of the image of the structure being evaluated. The resolution of the image or outline of any anomaly may be increased by adding additional pitch-catch wave paths enclosing the anomaly.

FIG. 5 illustrates an example of generating an image 500 of an anomaly 502 in a structure using a pulse-echo or self-sensing configuration in accordance with an embodiment of the present disclosure. Similar to that previously described, in a pulse-echo or self-sensing configuration or mode, each sensor 504 of a plurality of sensors 504 generates an individual pulse wave or Lamb wave. The same sensor 504 that generates the pulse wave collects the scattered wave data resulting from the pulse wave impinging on any anomaly or other feature of the structure. In the pulse-echo mode, each sensor 504 generates a substantially circular-shaped pulse-echo wave path 506a-506d as illustrated in FIG. 5 to generate a two dimensional image 500 of any anomaly based on a time-of-flight of any backscattered waves. The shape of each of the pulse-echo wave paths 506a-506d may be determined by a wave velocity profile as a function of a wave propagation angle and a measured time-of-flight of the backscattered waves. The pulse-echo wave paths 506a-506d are overlapped or superimposed on one another over the portion of the structure being evaluated to generate the outline 508 or two dimensional image of any anomaly 502. As illustrate in FIG. 5, the outline 508 of the anomaly 502 corresponds to an area of most overlapping backscattered wave data of the circular-shaped pulse wave paths 506a-506d. This area will appear visually contrasted as illustrated in FIG. 5 relative to other portions or areas of the image of the structure being evaluated. Similar to the pitch-catch configuration, the more pulse-echo wave paths that are available to enclose any anomaly, the better the resolution of the image or outline of the anomaly. If the system is capable of both pitch-catch and pulse-echo configurations, all pitch-catch and pulse-echo paths can be combined and superimposed on one another by the same procedure. The present disclosure may also include a structural health monitoring system consisting of distributed transmitters and sensors that may be permanently or temporarily attached to the structure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," and "includes" and/or "including" when used in this specification, specify the presence of stated features, integers, steps, operations, elements, and/or components, but do not preclude the presence or addition of one or more other features, integers, steps, operations, elements, components, and/or groups thereof.

Although specific embodiments have been illustrated and described herein, those of ordinary skill in the art appreciate that any arrangement which is calculated to achieve the same purpose may be substituted for the specific embodiments shown and that the disclosure has other applications in other environments. This application is intended to cover any adaptations or variations of the present disclosure. The following claims are in no way intended to limit the scope of the disclosure to the specific embodiments described herein.

What is claimed is:

1. A method for generating an image of an anomaly, comprising:
   generating a pulse wave into a structure being evaluated from each of a plurality of sensors;
   collecting any scattered wave data caused by the pulse wave impacting an anomaly, wherein the scattered wave data is collected by the same sensor that generated the pulse wave or by a different sensor;
   identifying any backscattered wave data from any anomaly in the structure;
   processing the backscattered wave data from each of the sensors collecting the scattered wave data to generate a two dimensional image of any anomaly, wherein processing the backscattered wave data comprises superimposing the backscattered wave data from each of the sensors that collected the scattered wave data to generate an image of any anomaly; and
   presenting the two dimensional image of any anomaly.

2. The method of claim 1, wherein an outline of any anomaly corresponds to an area of most overlapping backscattered wave data which appears visually contrasted relative to other portions of an image of the structure being evaluated.

3. The method of claim 1, further comprising:
   generating baseline wave data for the structure; and
   calibrating a velocity of propagation of waves in the structure by using at least one of the baseline wave data, an analytical model, and a FEM model.

4. The method of claim 1, further comprising:
   performing signal processing on only the backscattered wave data using the baseline wave data for the structure; and
   using at least one of mode decomposition and noise cancellation to identify the backscattered waves.

5. The method of claim 1, wherein the plurality of sensors comprises a multiplicity of actuators, each for generating a pulse wave, and a multiplicity of receiving sensors, each for collecting scattered wave data, the multiplicity of actuators and the multiplicity of receiving sensors each being positioned at selected locations on the structure relative to one another to generate the two dimensional image of the anomaly.

6. The method of claim 1, wherein the structure is one of an aircraft, a terrestrial vehicle, a watercraft, and a civil structure.

7. The method of claim 1, further comprising operating in one of a pitch-catch mode and a pulse-echo mode to generate the two dimensional image of any anomaly, wherein the pitch-catch mode comprises generating the pulse wave by each of selected ones of the plurality of sensors being actuators and collecting the scattered wave data by each of other selected ones of plurality of sensors, each actuator-sensor pair forming a pitch-catch pulse wave path, and the pulse-echo mode comprises generating the pulse wave by each of the plurality of sensors and collecting the scattered wave data by the same sensor that generated the pulse wave.

8. The method of claim 1, further comprising operating in a pitch-catch configuration, wherein selected ones of the plurality of sensors are actuators, each actuator generating a separate pulse wave and other selected ones of the plurality of sensors collecting the scattered wave data, each actuator-sensor pair defining an actuator-sensor pulse wave path.

9. The method of claim 8, further comprising generating a multiplicity of substantially ellipsoid-shaped actuator-sensor pulse wave paths to generate the two dimensional image of any anomaly based on a time-of-flight of any backscattered waves, and superimposing the actuator-sensor pulse wave paths on one another over a portion of the structure being evaluated to generate the two dimensional image of any anomaly, wherein a shape of each actuator-sensor pulse wave path being determined by a wave velocity profile as a function of a wave propagation angle and a measured time-of-flight of the backscattered waves.

10. The method of claim 1, further comprising operating in a pulse-echo or self-sensing configuration, wherein each of the plurality of sensors generates an individual pulse wave and the same sensor collects any backscattered wave data to define a pulse-echo path.

11. The method of claim 10, further comprising generating a multiplicity of substantially circular-shaped pulse-echo paths to generate the two dimensional image of any anomaly based on a time-of-flight of any backscattered waves, and superimposing the pulse-echo paths on one another over a portion of the structure being evaluated to generate the two dimensional image of any anomaly, wherein a shape of each of the pulse-echo paths being determined by a wave velocity profile as a function of a wave propagation angle and a measured time-of-flight of the backscattered waves.

12. A method for generating an image of an anomaly, comprising:
generating a pulse wave into the structure being evaluated from each of the plurality of sensors positioned at predetermined locations on a portion a structure being evaluated;
collecting any scattered wave data caused by the pulse wave impacting an anomaly, wherein the scattered wave data is collected by the same sensor that generated the pulse wave or by a different sensor;
identifying any backscattered wave data from a distal edge of any anomaly relative to a location of the sensor collecting the scattered wave data;
processing the backscattered wave data from each of the sensors collecting the scattered wave data to generate a two dimensional image of any anomaly in the structure being evaluated, wherein processing the backscattered wave data comprises superimposing the backscattered wave data from each of the sensors that collected the scattered wave data, wherein an outline of any anomaly corresponds to an area of most overlapping backscattered wave data which appears visually contrasted relative to other portions in the two dimensional image of the structure being evaluated; and
presenting the two dimensional image of any anomaly.

13. The method of claim 12, further comprising operating in a pitch-catch configuration, wherein selected ones of the plurality of sensors are actuators, each actuator generating a separate pulse wave and other selected ones of the plurality of sensors collecting the scattered wave data, each actuator-sensor pair defining an actuator-sensor pulse wave path.

14. The method of claim 13, further comprising generating a multiplicity of substantially ellipsoid-shaped actuator-sensor pulse wave paths to generate the two dimensional image of any anomaly based on a time-of-flight of any backscattered waves, and superimposing the actuator-sensor pulse wave paths on one another over a portion of the structure being evaluated to generate the two dimensional image of any anomaly, wherein a shape of each actuator-sensor pulse wave path being determined by a wave velocity profile as a function of a wave propagation angle and a measured time-of-flight of the backscattered waves.

15. The method of claim 12, further comprising operating in a pulse-echo or self-sensing configuration, wherein each of the plurality of sensors generates an individual pulse wave and the same sensor collects any backscattered wave data to define a pulse-echo path.

16. The method of claim 15, further comprising generating a multiplicity of substantially circular-shaped pulse-echo wave paths to generate the two dimensional image of any anomaly based on a time-of-flight of any backscattered waves, and superimposing the pulse-echo wave paths on one another over a portion of the structure being evaluated to generate the two dimensional image of any anomaly, wherein a shape of each of the pulse-echo paths being determined by a wave velocity profile as a function of a wave propagation angle and a measured time-of-flight of the backscattered waves.

17. A system for generating an image of an anomaly, comprising:
a plurality of devices, each for generating a pulse wave into a structure being evaluated and for collecting any scattered wave data caused by energy of the pulse wave being at least partially reflected by any anomaly; and
a structural health monitoring unit for generating a two dimensional image of any anomaly in the structure being evaluated from backscattered wave data from any anomaly, wherein the structural health monitoring unit comprises a module for processing the backscattered wave data by superimposing the backscattered wave data from each of the devices that collected the scattered wave data to generate an image of any anomaly.

18. The system of claim 17, wherein an outline of any anomaly corresponds to an area of most overlapping backscattered wave data which appears visually contrasted relative to other portions in the two dimensional image of the structure being evaluated.

19. The system of claim 17, wherein the plurality of devices are configured for operation in one of a pulse-echo mode and a pitch-catch mode.

20. The system of claim 19, wherein in the pitch-catch mode, the plurality of devices comprises:
a plurality of actuators, each actuator for generating a separate pulse wave in the structure being evaluated; and
a plurality of sensors, each sensor for collecting the scattered wave data, the plurality of actuators and the plurality of sensors being paired to form actuator-sensor pairs.

21. The system of claim 20, wherein each actuator-sensor pair being adapted to generate a substantially ellipsoid-shaped actuator-sensor pulse wave path to generate the two dimensional image of any anomaly based on a time-of-flight of any backscattered waves, and wherein the structural health monitoring unit comprises a module to superimpose each of the actuator-sensor pulse wave paths on one another over a portion of the structure being evaluated to generate the two dimensional image of any anomaly, wherein a shape of each actuator-sensor pulse wave path being determined by a wave velocity profile as a function of a wave propagation angle and a measured time-of-flight of the backscattered waves.

22. The system of claim 19, wherein in the pulse-echo mode, the plurality of devices comprise a plurality of sensors, each sensor generating an individual pulse wave and the same sensor collecting any backscattered wave data from the individual pulse wave generated by the sensor.

23. The system of claim 22, wherein each of the plurality of sensors generating a substantially circular-shaped pulse-echo pulse wave path to generate the two dimensional image of any anomaly based on a time-of-flight of any backscattered waves, and wherein the structural health monitoring unit comprises a module to superimpose the pulse-echo pulse wave paths on one another over a portion of the structure being evaluated to generate the two dimensional image of any anomaly, wherein a shape of each of the pulse-echo pulse wave paths being determined by a wave velocity profile as a function of a wave propagation angle and a measured time-of-flight of the backscattered waves.

24. A system for generating an image of an anomaly, comprising:
- a plurality of actuators, each positioned at a predetermined location on a portion of a structure being evaluated, and each actuator for generating a pulse wave into the structure;
- a plurality of sensors, each positioned at a selected location on the portion of the structure being evaluated, and each sensor for collecting any scattered wave data caused by energy of the pulse wave being at least partially reflected by an anomaly;
- a structural health monitoring unit for identifying any backscattered wave data from a distal edge of any anomaly relative to a location of the sensor collecting the scattered wave data and for processing the backscattered wave data from each of the sensors collecting the scattered wave data to generate a two dimensional image of any anomaly, wherein the structural health monitoring unit processes the backscattered wave data by superimposing the backscattered wave data from each of the sensors that collected the scattered wave data to generate an image of any anomaly; and
- an output device for presenting the two dimensional image of any anomaly.

25. The system of claim 24, wherein an outline of any anomaly corresponds to an area of most overlapping backscattered wave data which appears visually contrasted relative to other portions of the image.

* * * * *